(12) United States Patent
Iwasaki et al.

(10) Patent No.: US 8,105,060 B2
(45) Date of Patent: Jan. 31, 2012

(54) IMPACT TARGET CAPSULE AND IMPACT COMPRESSION APPARATUS

(75) Inventors: Hideharu Iwasaki, Kurashiki (JP); Takayuki Ikeda, Kurashiki (JP); Hideaki Fujiwara, Kurashiki (JP); Yoshihisa Tsuji, Kurashiki (JP)

(73) Assignee: Kuraray Co., Ltd., Kurashiki-shi (JP)

( * ) Notice: Subject to any disclaimer, the term of this patent is extended or adjusted under 35 U.S.C. 154(b) by 122 days.

(21) Appl. No.: 12/438,046

(22) PCT Filed: Aug. 31, 2007

(86) PCT No.: PCT/JP2007/066992
§ 371 (c)(1),
(2), (4) Date: Feb. 19, 2009

(87) PCT Pub. No.: WO2008/029726
PCT Pub. Date: Mar. 13, 2008

(65) Prior Publication Data
US 2009/0232921 A1 Sep. 17, 2009

(30) Foreign Application Priority Data
Sep. 1, 2006 (JP) .................. 2006-237869

(51) Int. Cl.
*B29C 43/02* (2006.01)
(52) U.S. Cl. .............. 425/1; 425/78; 425/416; 249/122; 249/160
(58) Field of Classification Search ............... 425/1, 77, 425/78, 411–412; 249/120–122, 140, 144, 249/154, 164; 264/84
See application file for complete search history.

(56) References Cited

U.S. PATENT DOCUMENTS

| 4,013,259 A | * | 3/1977 | Tryon | 249/57 |
| 4,497,873 A | * | 2/1985 | Barker | 425/77 |
| 4,599,060 A | * | 7/1986 | Flinn et al. | 425/1 |
| 4,717,627 A | | 1/1988 | Nellis et al. | |
| 4,762,754 A | | 8/1988 | Nellis et al. | |
| 4,907,731 A | | 3/1990 | Nellis et al. | |
| 4,925,501 A | * | 5/1990 | Harasek | 264/84 |

(Continued)

FOREIGN PATENT DOCUMENTS
JP 40 3010 2/1965
(Continued)

OTHER PUBLICATIONS

Materia, vol. 44, No. 4, pp. 296-301, (2005), (with partial English translation).

*Primary Examiner* — Richard Crispino
*Assistant Examiner* — Thukhanh Nguyen
(74) *Attorney, Agent, or Firm* — Oblon, Spivak, McClelland, Maier & Neustadt, L.L.P.

(57) ABSTRACT

A target capsule includes (A) a pedestal having a central projection, (B) a pedestal aid attached to the central projection so as to define a sample-loading assembly, and (C) an impact-receiving member, wherein the components (A), (B), and (C) are detachable from each other. The impact target capsule can be readily loaded with a sample, allows the sample to be easily retrieved after application of impact pressure, and can be used repeatedly, and thereby the capsule can be preferably used as an impact compression apparatus in combination with a single-stage powder gun or a single-stage gas gun.

14 Claims, 6 Drawing Sheets

U.S. PATENT DOCUMENTS

| | | | |
|---|---|---|---|
| 5,087,435 A * | 2/1992 | Potter et al. | 423/446 |
| 5,425,818 A * | 6/1995 | Hirosawa et al. | 264/84 |
| 6,010,659 A * | 1/2000 | Gentsch et al. | 425/78 |
| 2003/0047299 A1* | 3/2003 | Ma | 164/376 |

FOREIGN PATENT DOCUMENTS

| | | |
|---|---|---|
| JP | 55 56008 | 4/1980 |
| JP | 59 165112 | 9/1984 |
| JP | 63 153202 | 6/1988 |
| JP | 2 237634 | 9/1990 |
| JP | 4 202045 | 7/1992 |
| JP | 6 134284 | 5/1994 |
| JP | 9 220463 | 8/1997 |
| JP | 10 29814 | 2/1998 |
| JP | 11 189853 | 7/1999 |
| JP | 2001 54731 | 2/2001 |

\* cited by examiner

IMPACT TARGET CAPSULE AND IMPACT COMPRESSION APPARATUS

FIELD OF THE INVENTION

The present invention relates to an impact target capsule and an impact compression apparatus, and in particular, to an impact target capsule including components that are detachable from each other and an impact compression apparatus that is a combination of the capsule and a single-stage powder gun. Since the impact target capsule includes components that are detachable from each other, the capsule can be reused repeatedly through disassembly and assembly after subjected to impact. Accordingly, the capsule can be preferably used as an impact compression apparatus in combination with a single-stage powder gun or a single-stage gas gun.

BACKGROUND OF THE INVENTION

A solid article has been commonly formed by applying impact pressure to fine particles that allows the temperature of the particles to increase instantaneously. For example, well known are a method of manufacturing diamond artificially (Patent Document 1), a method of manufacturing an oxide superconductive material (Patent Document 2), a method of manufacturing a giant magnetostriction device (Patent Document 3), and a method of manufacturing a magnet (Nonpatent Document 1).

However, these disclosed methods barely refer to a target capsule for storing a sample to be subjected to impact. Non-patent Document 1 describes a threaded target capsule used for holding a sample to be subjected to impact. Unfortunately, this type of target capsule must be inevitably destroyed to retrieve a sample after the impact.

Patent Document 1: Japanese Unexamined Patent Application Publication No. 6-134284
Patent Document 2: Japanese Unexamined Patent Application Publication No. 4-202045
Patent Document 3: Japanese Unexamined Patent Application Publication No. 11-189853
Non-patent Document 1: Material Vol. 44, No. 4, 2005, pp. 296-301

DISCLOSURE OF THE INVENTION

Problems to be Solved by the Invention

Accordingly, an object of the present invention is to provide a target capsule that can be readily loaded with a sample, that allows the sample to be easily retrieved after applying impact pressure, and that can be used repeatedly, on the modification of a substance by application of impact pressure.

Means for Solving the Problems

The inventors have reached the invention through extensive study to achieve the object. The present invention provides an impact target capsule including (A) a pedestal having a central projection, (B) a pedestal aid attached to the central projection so as to define a sample-loading assembly, and (C) an impact-receiving member, more specifically, an impact target capsule essentially including (A) a pedestal having a central projection, (B) a pedestal aid attached to the central projection so as to define a sample-loading assembly, and (C) an impact-receiving member, wherein the elements (A), (B), and (C) are detachable from each other.

Another aspect of the present invention provides an impact target capsule including (A) a pedestal having a central projection and (C) an impact-receiving member, more specifically an impact target capsule essentially including (A) a pedestal having a central projection and (C) an impact-receiving member, wherein the one side of the impact-receiving member (C) faces the pedestal, and is attached to the projection so as to define a sample-loading assembly, and the elements (A) and (C) are detachable from each other.

A further aspect of the present invention provides an impact compression apparatus including the impact target capsule and a single-stage powder gun or a single-stage gas gun.

Advantages of the Invention

The present invention can provide an impact target capsule. In the impact target capsule of the present invention, a sample can be readily loaded into the impact target capsule and can be easily retrieved from the impact target capsule after application of impact pressure. Besides, the target capsule can be used repeatedly. Accordingly, the capsule can be preferably used as an impact compression apparatus in combination with a single-stage powder gun or a single-stage gas gun.

The target capsule of the present invention is particularly suitable for repeated use when a single-stage powder gun is used under the condition of a flight distance of 2 to 15 m and a flight speed of 500 to 2000 m/s or when a single-stage gas gun is used under the condition of a flight distance of 2 to 10 m and a flight speed of 50 to 1000 m/s. In general, the generated impact pressure is about 10 to about 50 GPa in the single-stage powder gun and about 0.01 to about 15 GPa in the single-stage gas gun, although depending on the material of the flying object.

Figure 1:
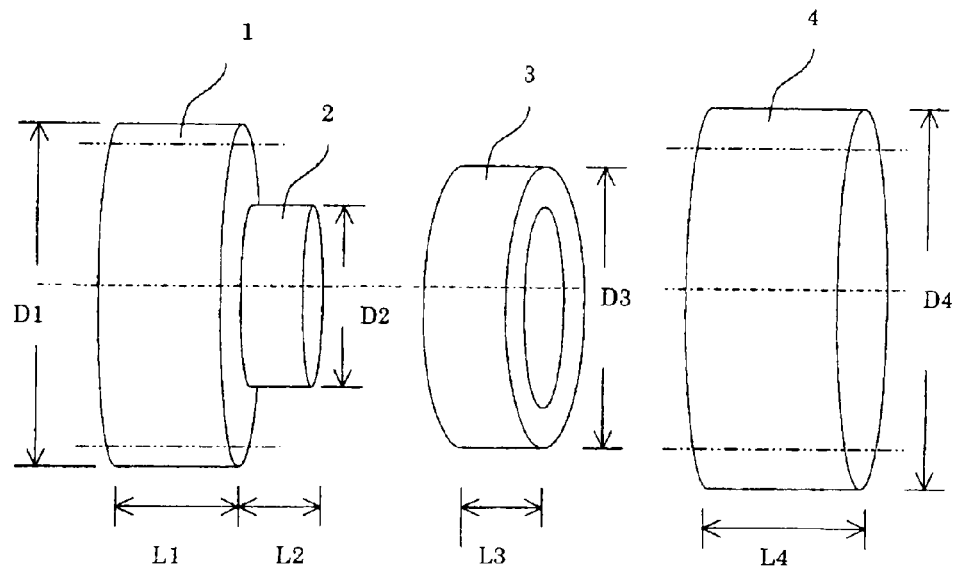
FIG. 1 is a schematic view of a target capsule in accordance with an embodiment of the present invention.

EXPLANATIONS OF REFERENCE NUMERALS 1 pedestal
2 central projection
3 pedestal aid
4 impact-receiving member
5 cavity
6 momentum trap
7 pedestal
8 impact-receiving member
9 central projection
10 pedestal aid
11 protective ring 12 impact-inducing member
13 bolt hole

BEST MODE FOR CARRYING OUT THE INVENTION

An impact target capsule of the present invention is described below in detail with reference to the drawings. FIG. 1 is a schematic view of the impact target capsule of the present invention. The capsule essentially includes (A) a pedestal having a central projection 1, (B) a pedestal aid 3 attached to the central projection 2 with no gap so as to define a sample-loading assembly, and (C) an impact-receiving member. Although these shapes are not particularly limited, a circular shape is explained in detail below because circular objects can be easily manufactured, is suitable for practical use, and has high mechanical strength.

In the impact target capsule of the present invention, (A) the pedestal having a central projection, (B) the pedestal aid attached to the central projection with no gap so as to define a sample-loading assembly, and (C) the impact-receiving member are detachable from each other. Giving consideration to the practical size of a single-stage powder gun or a single-stage gas gun, in general, the pedestal has a diameter D1 in the range of about 10 to about 200 mm and has a thickness L1 in the range of about 2 to about 20 mm, while the central projection has a diameter D2 in the range of about 8 to about 160 mm and a height L2 in the range of about 2 to about 50 mm.

The pedestal aid is attached to the central projection with no gap so as to define a sample-loading assembly. Using this pedestal aid, a target capsule can be assembled in response to a slight error in shaping of a sample. The pedestal aid is desirably composed of the same material as that of the pedestal and impact-receiving member. Preferably, the pedestal aid has a diameter D3 in the range of about 9 to about 190 mm and a thickness L3 that satisfies D3<D1. The impact-receiving member has a cavity 5, if required, and L4 generally ranges from about 2 to about 60 mm (the cavity, if provided, generally has a depth L5 of not more than 59 mm). To load a sample, L3>L2 is required, and the thickness of the sample is determined by L3-L2.

The thickness L3 of the pedestal aid is not particularly limited in so far as the pedestal aid can endure the impact from a flying object. However, an excess reduction in the thickness causes low mechanical strength while an excess increase in the thickness causes poor handling due to a significant increase in weight. For this reason, the range of the thickness is preferably 3 to 50 mm, and more preferably 5 to 30 mm.

The thickness of a sample, which depends on impact to be applied, should not be easily defined. An excess increase in the thickness is not desirable because the impact is not evenly applied to the sample. Preferably, the thickness of the sample is the same as the thickness of the stunning plane of a flying object, the stunning plane applying shock waves. Accordingly, the thickness preferably ranges from 0.01 to 20 mm, and more preferably from 0.02 to 18 mm.

The sample is preliminarily tabletted into a given thickness before loading. The method of making the tablet is not limited, but the sample must be tabletted into a shape that can be loaded so as to be put into close contact with the projection and pedestal aid. The area of the base of the tablet is substantially the same as that of the projection. If the area is significantly large, shock waves do not propagate into the tablet sufficiently and the homogeneity of the sample may be impaired. For this reason, the area of the base of the tablet is equal to or slightly less than that of the stunning plane of the flying object. The area of the base of the tablet ranges preferably from 30 to 100%, more preferably 40 to 90%, and most preferably 50 to 80% of the stunning plane of the flying object in consideration of the homogeneity of a sample.

Figure 2:
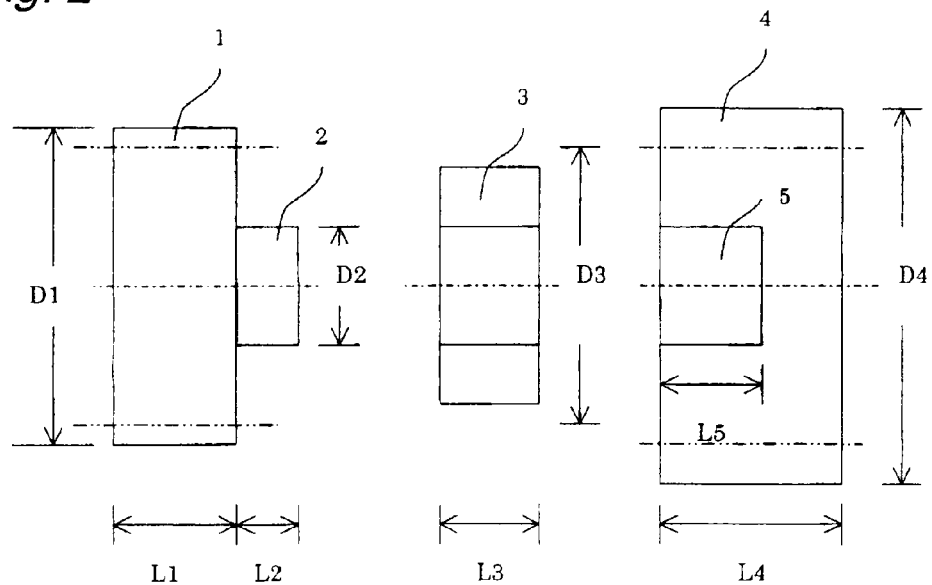
FIG. 2 is a schematic cross-sectional view of a target capsule in accordance with another embodiment of the present invention.

The sample is loaded so as to put into close contact with the projection and the pedestal aid. For example, as shown in FIG. 1, the sample is loaded into an annular space defined by L3-L2 and the pedestal aid that attached to the projection. FIG. 2 is a cross-sectional front view showing another exemplary target capsule including a pedestal 1, a pedestal aid 2, and an impact-receiving member 3, the impact-receiving member having a cavity 5. In FIG. 2, the thickness of the sample is defined by L3-L2+L5.

Figure 3:
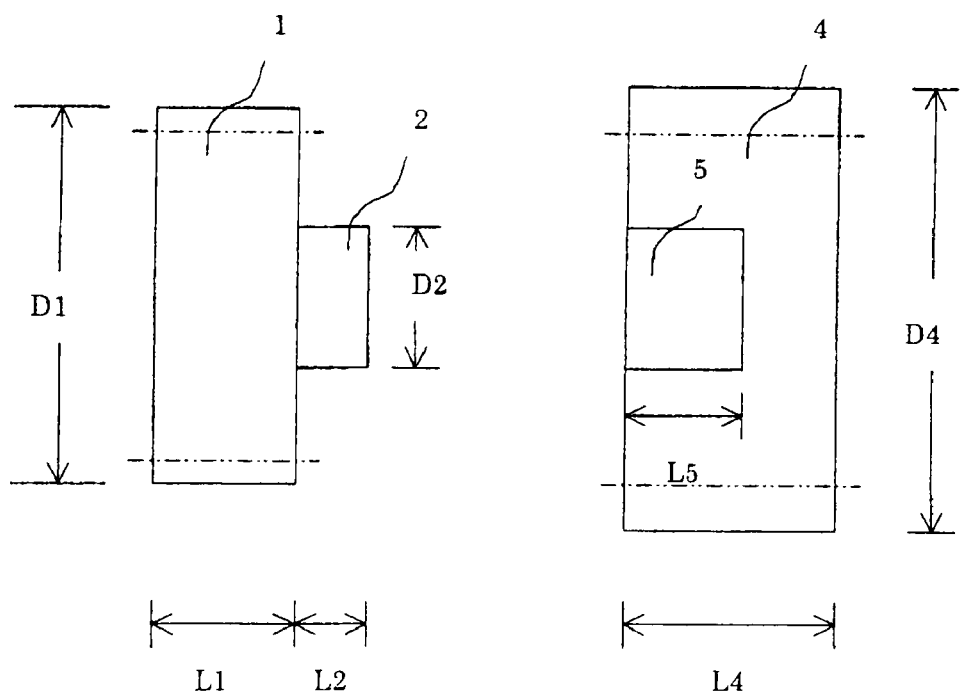
FIG. 3 is a schematic cross-sectional view of a target capsule without a pedestal aid.

FIG. 3 is another exemplary target capsule that does not include a pedestal aid, its impact-receiving member having a cavity. In this case, the sample is loaded into the space that is defined by L5-L2 and the cavity 5.

Preferably, the impact-receiving member has a diameter D4 and a thickness L4 that satisfies D4>D3. However, at an excessively small thickness, the component cannot absorb the impact caused by collision with the flying object. At an excessively large thickness, the weight undesirably increases. For this reason, the thickness ranges preferably from 0.1 to 30 mm, and more preferably from 0.2 to 20 mm.

In the impact-receiving member having the cavity, the thickness L4-L5 should not be easily defined because the thickness depends on the material and the thickness of the stunning plane of the flying object. However, at a significantly large thickness, shock waves readily diffuse. At a significantly small thickness, the sample cannot be retrieved in some cases because the impact-receiving member is destroyed by the shock waves. Preferably, the thickness L4-L5 should be equal to or less than that of the stunning plane of the flying object under the condition that the material of the impact-receiving member is the same as that of the stunning plane of the flying object. Based on this standpoint, the thickness L4-L5 preferably ranges from 20 to 120%, and more preferably from 40 to 110% of the stunning plane of the flying object.

Under the condition that the material of the stunning plane of the flying object is harder than that of the impact-receiving member, the thickness L4-L5 ranges preferably from 50 to 140%, and more preferably from 60 to 120% of the stunning plane of the flying object because the impact-receiving member is more readily destroyed by the impact.

The impact-receiving member and the pedestal aid can be integrated or separated from each other. The diameter D4 of the impact-receiving member is preferably determined such that the cross-sectional area of the impact-receiving member is larger than that of the flying object. The cross-sectional area of the impact-receiving member ranges preferably from one to three times, and more preferably ranges from one to two times that of the flying object.

Figure 4:
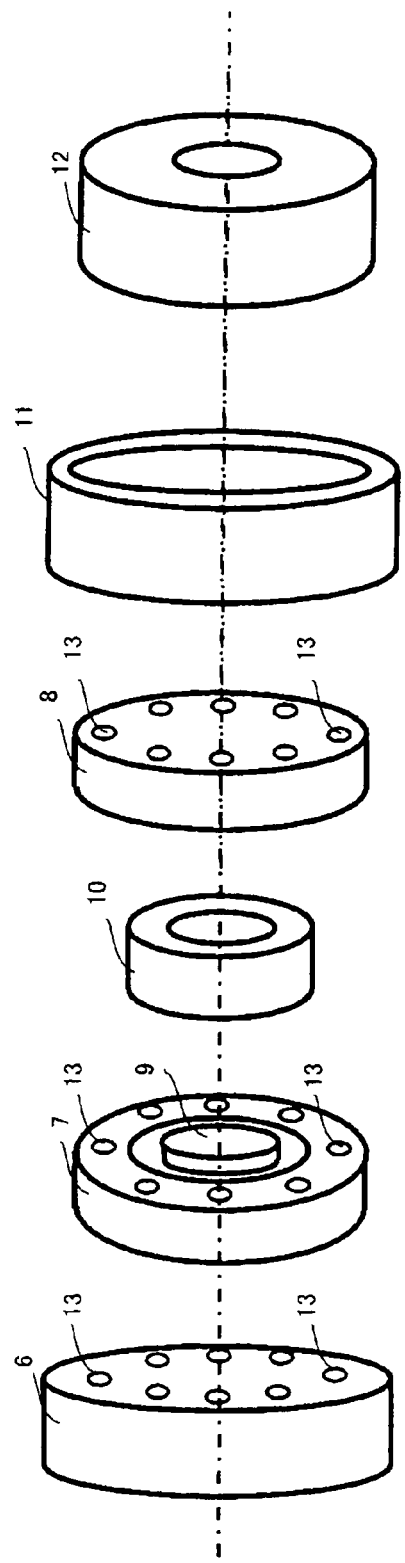
FIG. 4 is a schematic view of a target capsule in accordance with another embodiment of the present invention.

FIG. 4 shows another exemplary disassembled target capsule, and is a schematic view showing the order of assembly of the capsule from the left. In FIG. 4, a momentum trap 6 plays a role in preventing the capsule from being destroyed by diffusing kinetic momentum that occurs during the impact pressure, to its periphery. In FIG. 4, a pedestal 7 and an impact-receiving member 8 have the same shape, and constitute a pair of components. A sample-loading assembly consists of the pair of the pedestal and impact-receiving member, and a pedestal aid 10 that is attached to central projections 9 provided on the pedestal and the impact-receiving member, respectively. In addition, the assembly of the pair of the pedestal and impact-receiving member and the pedestal aid is fit into a protective ring 11. The protective ring prevents the impact-receiving member from lateral expansion causing diffusion of the shock waves by the impact.

Figure 5:
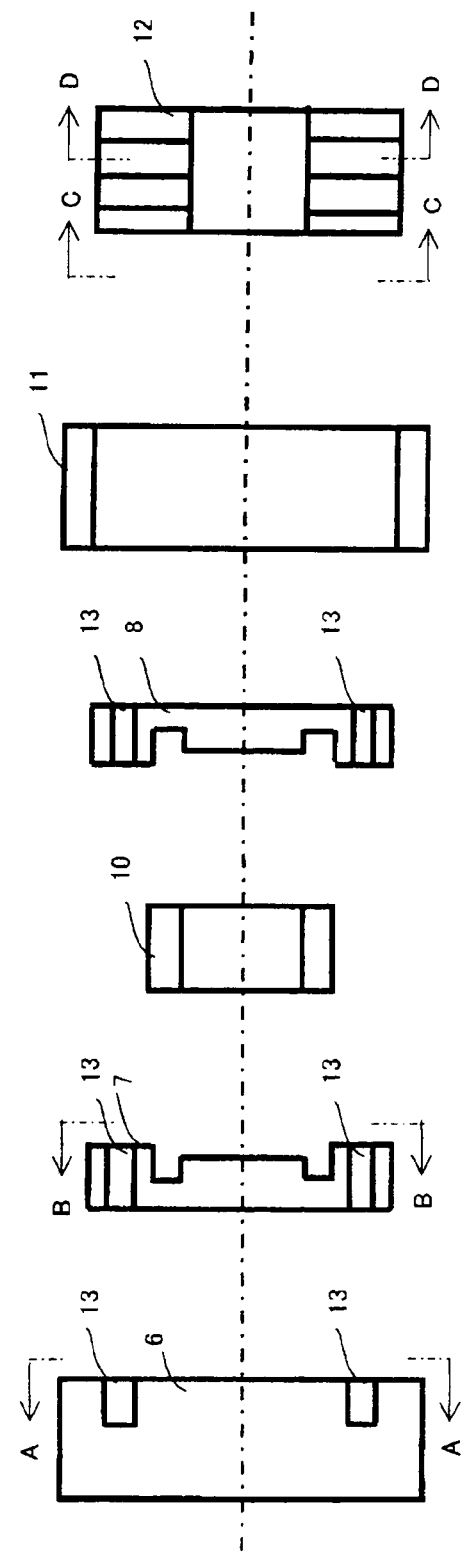
FIG. 5 is a schematic cross-sectional view of the target capsule shown in FIG. 4.
Figure 6:
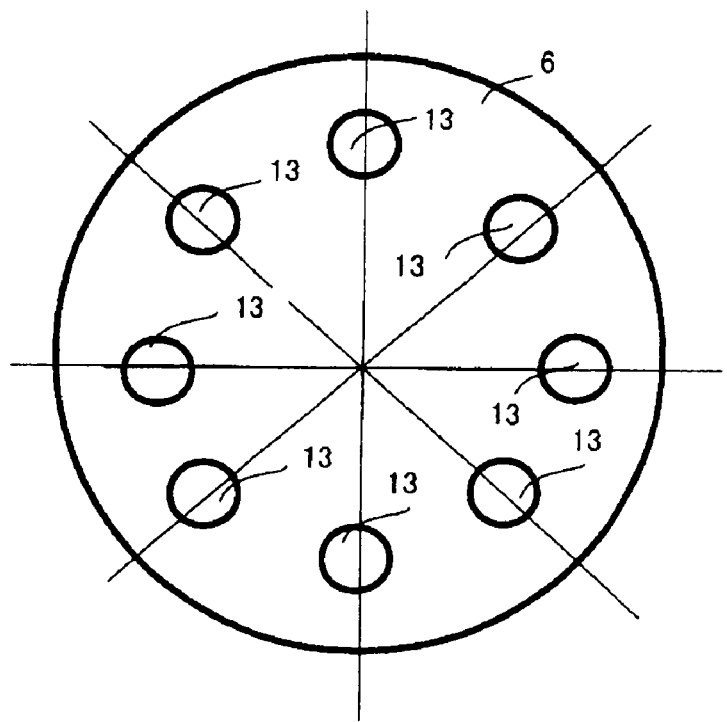
FIG. 6 is a view in the direction of arrows A-A in FIG. 5.
Figure 7:
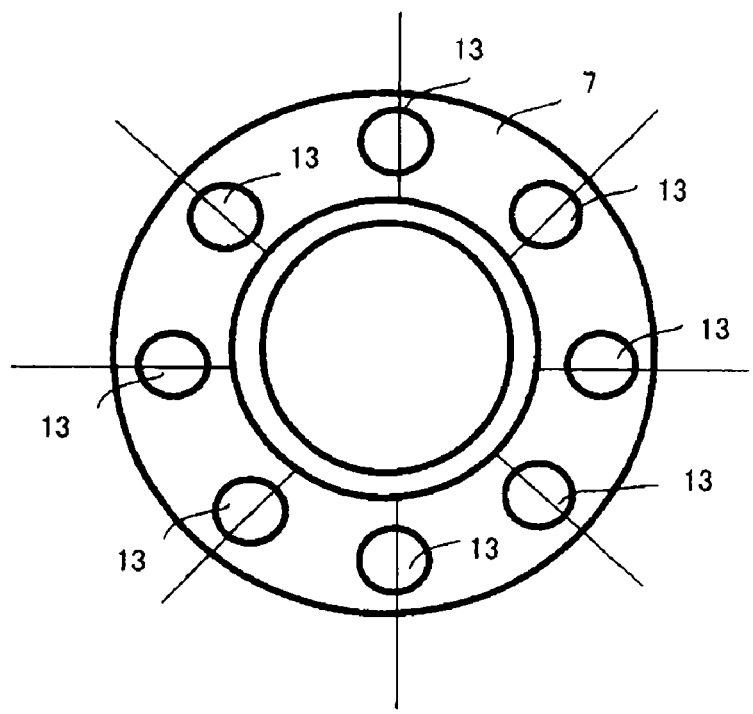
FIG. 7 is a view in the direction of arrows B-B in FIG. 5.
Figure 8:
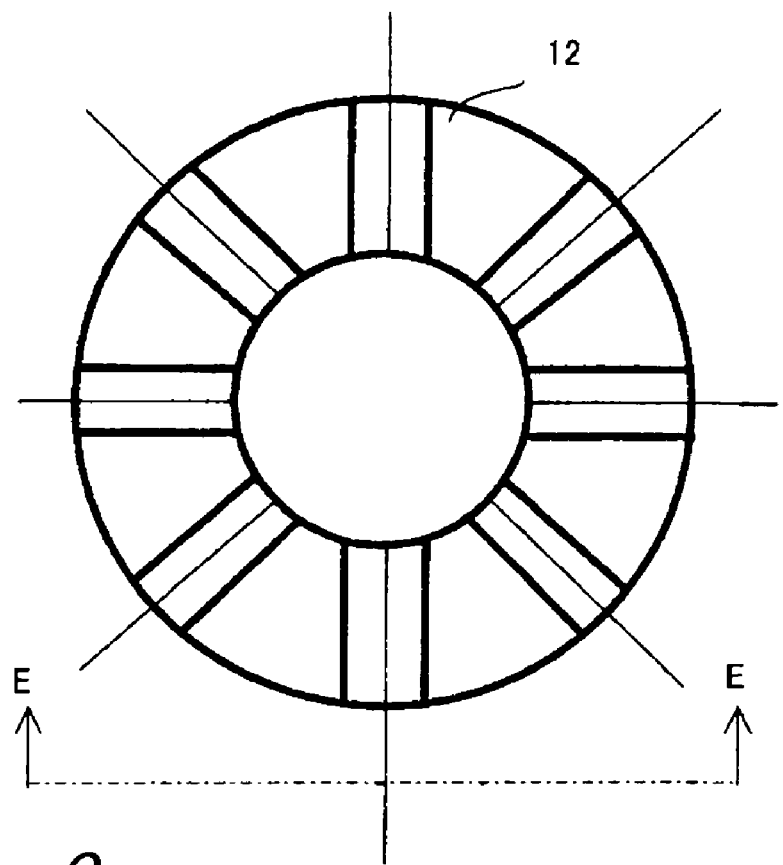
FIG. 8 is views in the direction of arrows C-C and D-D in FIG. 5.
Figure 9:
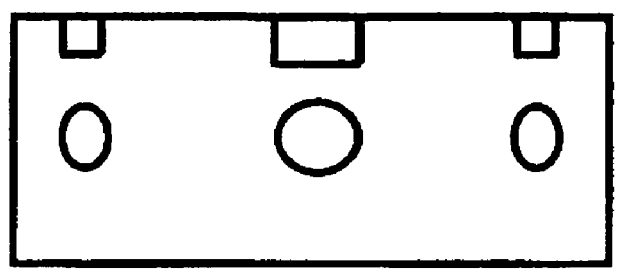
FIG. 9 is a view in the direction of arrows E-E in FIG. 8.

FIG. 5 is a schematic cross-sectional view of the target capsule shown in FIG. 4. FIGS. 6 and 7 are views in the direction of the arrows A-A and B-B, respectively, in FIG. 5. In FIG. 4 or FIG. 5, the impact-receiving member 8 is directly subjected to impact from the flying object. An impact-inducing member 12 has preferably gas holes and/or gas grooves to release gas that interferes with transmission of the shock waves occurring in a gunpowder, or a powder gun or a light gas gun. FIGS. 5, 8, and 9 illustrates examples in which eight grooves are disposed radially on the side of the pedestal of the impact-inducing member, and gas holes are disposed radially in parallel with the grooves, to release unnecessary gas from the interior to the exterior of the impact-inducing member that interferes with transmission of the shock waves through the impact-inducing member. The shape and the size of the holes and grooves are not limited since they are disposed to release the shock waves. Bolt holes 13 that are disposed in the momentum trap hold the bolts that are stuck out from the pedestal when the sample-loading assembly consisting of the pair of the pedestal and impact-receiving member, and the pedestal aid are fixed to each other with the bolts after loading the sample into the assembly.

The diameter and the thickness of the pedestal, and the diameter and the height of the projection, as illustrated in FIG. 1, are not particularly limited in so far as the sample-loading assembly is formed with the pair of the pedestal and the impact-receiving member and the pedestal aid that is attached to the central projection on each pedestal. FIGS. 4 through 9 are schematic views of the target capsule, the momentum strap and protective ring being also not particularly limited.

In the present invention, the materials of the pedestal, the pedestal aid, and the impact-receiving member are not particularly limited in so far as they can endure shock waves. In general, ordinary steel, alloy steel, cast iron, stainless steel, heat-resisting steel, copper, copper alloy, aluminium, aluminium alloy, nickel, nickel alloy, titanium, and cobalt alloy are used. Tungsten can also be used to enhance impact strength. In the case of using an expensive material, such a material can be used only for the stunning plane. Rolled structural steels such as iron and copper alloys such as brass are commonly used due to ease of manufacture.

The sample is placed between the projection and the pedestal aid with close contact. Coating of the surfaces, in contact with the sample, of the components is desirable. This can prevents metal such as iron, which is derived form the material on the surfaces of the components, being mixed into the sample as an impurity. Examples of the material usable for the coating include organic polymer compounds such as polyolefins, e.g., polyethylene and polypropylene, polyesters, e.g., polyethylene terephthalate and polybutylene terephthalate, hydroxyl-containing polymers, e.g., polyvinyl alcohol and polyethylene-vinyl alcohol copolymers, fluorine-containing polymers, e.g., polyvinylidene fluoride and polytetrafluoroethylene; metal oxides such as silica, alumina, and titania; and metals such as copper, aluminium, zinc, silver, and gold.

Although the approach to the coating is not particularly limited, the following approaches can be employed: an approach involving application and dryness of solution, an approach involving application and dryness of sol solution, an approach involving use of a film or a foil, and an approach involving formation of a film by spraying particulate material. The thickness of the coating ranges generally from 1 µm to 1 mm, from 10 to 800 µm, and more preferably from 20 to 700 µm in consideration of attenuation of the impulse force, although it depends on the impulse force.

The pedestal, the pedestal aid, and the impact-receiving member are aligned with the central axis, as shown in the drawings, such that the shock waves propagate horizontally. Hence, the shock waves propagate into the sample when the flying object that is shot from a single-stage powder gun or a single-stage gas gun hits against the impact-receiving member at a substantially right angle. If any one of these components is not aligned with the central axis, the shock waves do not propagate horizontally but diffuse undesirably. After the sample is loaded, the pedestal, the pedestal aid, and the impact-receiving member are tightly fixed to each other with bolts for use. The present invention will be described in detail below with reference to the following examples, but which should not restrict the scope of the invention.

EXAMPLE 1

A target capsule made of iron (SS400) was produced such that each dimension in FIG. 2 was as follows: D1=60 mm, D2=20 mm, D3=50 mm, D4=60 mm, L1=10 mm, L2=11 mm, L3=12 mm, L4=4 mm, and L5=2 mm. Although not shown in the drawing, the pedestal 1 and the impact-receiving member 4 was able to be fixed to each other with bolts, and the pedestal aid 3 was able to be fixed between the pedestal 1 and impact-receiving member 4. In FIGS. 1 and 2, the two-dot chain lines show the placement of bolts on the fringes.

Hexagonal zinc sulfide "RAK-LC" manufactured by Sakai Chemical Industry Co., Ltd. was shaped into a tablet (weight: 3 g) having a diameter of 20 mm and a thickness of 3 mm, using a hydraulic molding machine (RIKEN POWER P-1B-041 manufactured by RIKEN SEIKI) under a pressure of 1 kg/cm$^2$.

The hexagonal zinc sulfide tablet was inserted into the target capsule, and the target capsule was assembled. The target capsule was attached to the shock wave generator TYPE 20 manufactured by GM Engineering Co., Ltd., and a flying object made of ABS (with a stunning plane made of copper, thickness: 2 mm, and diameter: 40 mm) was bombarded under vacuum to the target capsule at a speed of 500 m/s from a distance of 2 m. After the collision, the target capsule was retrieved, and then the components were disassembled to retrieve the zinc sulfide tablet (3 g). The retrieved zinc sulfide was analyzed by ICP spectrometry. The content of the iron derived from the inner surface of the target capsule was 2012 ppm. The above collision was performed repeatedly, and the target capsule was able to be reused repeatedly.

EXAMPLE 2

Collision was repeated as in Example 1 except that the target capsule having the following dimensions in FIG. 3 was used: D1=60 mm, D2=20 mm, D4=60 mm, L1=10 mm, L2=7 mm, L4=12 mm, and L5=10 mm. The target capsule was reused repeatedly. Although not shown in the drawing, the pedestal 1 and the impact-receiving member 4 was able to be tightly fixed to each other with bolts on the fringe of the each component. In FIG. 3, the two-dot chain lines show the placement of bolts on the fringes.

EXAMPLE 3

Using a fine heat-resistant TFE coat manufactured by Fine Chemical Japan Co., Ltd., polytetrafluoroethylene was evenly sprayed five times onto a surface, in contact with the zinc sulfide, of the target capsule used in Example 1. After coating, thermal curing is carried out at a temperature of 200° C. for 3 hours to form a coating having a thickness of 11 µm.

The shock waves are applied to the target capsule as in Example 1, and then the zinc sulfide tablet (3 g) was retrieved. The retrieved zinc sulfide was analyzed by ICP spectrometry. The content of iron in the tablet was 11 ppm.

EXAMPLE 4

In the target capsule used in Example 1, the surface in contact with zinc sulfide was coated with a polyvinyl alcohol film having a thickness of 40 μm. The shock waves were applied to the target capsule as in Example 1, and then the zinc sulfide tablet (3 g) was retrieved. The retrieved zinc sulfide was analyzed by ICP spectrometry. Iron was not detected from the tablet.

EXAMPLE 5

The target capsule made of iron (SS400) as shown in FIG. 4 having the following dimensions was prepared by assembling the following components: the momentum trap 6 with a diameter of 110 mm and a thickness of 16 mm, a pair of a pedestal 7 and an impact-receiving member 8 each having a central projection 9 with a diameter of 40 mm and a height of 3 mm in the center of a disc with a diameter of 100 mm and a thickness of 8 mm, and having circular grooves of a depth of 5 mm and a width of 10 mm around the central projection 9, a pedestal aid 10 having a diameter of 60 mm and a thickness of 10 mm, which was fitted into the grooves, a protective ring 11 having an external diameter of 110 mm, an internal diameter 100 mm, and a thickness of 16 mm, a impact-inducing member 12 having radial grooves having a width of 13 mm and a depth of 5 mm on a perforated disc having an external diameter of 100 mm and an internal diameter of 40 mm and having holes penetrating from the interior to the exterior of the disc and having a diameter of 10 mm and a length of about 30 mm in parallel with the gloves. A sample-loading assembly consisting of the pair of the pedestal and impact-receiving member, and the pedestal aid was loaded with a sample and was tightly fixed with bolts. Collision was repeated as in Example 1, and the target capsule was able to be reused repeatedly. The retrieved zinc sulfide (3 g) was analyzed by ICP spectrometry. The content of the iron in the tablet was 2334 ppm.

EXAMPLE 6

In the target capsule used in Example 5, a copper foil having a thickness of 2 μm was attached on the surface in contact with zinc sulfide. The shock waves are applied to the target capsule for repeated collision as in Example 5. The target capsule was able to be reused repeatedly. The retrieved zinc sulfide (3 g) was analyzed by ICP spectrometry. Iron was not detected from the tablet.

INDUSTRIAL APPLICABILITY

The present invention can provide a target capsule including components that are adapted to be detachable from each other. After receiving impact, the target capsule can be reused repeatedly through disassembly and assembly. Accordingly, the capsule can be used preferably as an impact compression apparatus in combination with a single-stage powder gun.

The invention claimed is:

1. A reusable impact target capsule, comprising:
   (A) a pedestal having a central projection and an annular groove surrounding the central projection;
   (B) a pedestal aid having a ring shape and fitted into the annular groove of the pedestal, so as to define a sample-loading assembly having a cavity for loading a powder sample formed between the central projection of the pedestal and an inner wall of the ring of the pedestal aid;
   (C) an impact-receiving member detachably mounted on the pedestal aid;
   wherein the elements (A), (B) and (C) are detachable from each other and the inner surfaces of the sample-loading assembly are coated with a coating.

2. The reusable impact target capsule of claim 1, wherein the impact-receiving member (C) has a non-penetrating cavity in the center thereof at the bottom of the pedestal aid, the cavity having the same cross-sectional area as that of the central projection.

3. A reusable impact target capsule, comprising:
   (A) a pedestal having a central projection; and
   (B) an impact-receiving member having a central cavity for receiving the central projection of the pedestal, so as to define a sample-loading assembly having a cavity for loading a powder sample formed between the central projection of the pedestal and the central cavity of the impact-receiving member;
   wherein the elements (A) and (B) are detachable from each other and the inner surfaces of the sample-loading assembly are coated with a coating.

4. The reusable impact target capsule of claim 1, wherein (A) the pedestal and (C) the impact-receiving member have the same shape.

5. The reusable impact target capsule of claim 1, further comprising an impact inducing member.

6. The reusable impact target capsule of claim 5, wherein the impact-inducing member has gas holes and/or gas grooves to release gas that interferes with transmission of the shock waves.

7. An impact compression apparatus comprising:
   the reusable impact target capsule of claim 1; and
   a single-stage powder gun, a single-stage gas gun, or gunpowder.

8. The impact compression apparatus of claim 7, wherein the reusable impact target capsule further comprises an impact inducing member.

9. The impact compression apparatus of claim 8, wherein the impact-inducing member has gas holes and/or gas grooves to release gas that interferes with transmission of the shock waves.

10. The reusable impact target capsule of claim 3, further comprising an impact inducing member.

11. The reusable impact target capsule of claim 10, wherein the impact-inducing member has gas holes and/or gas grooves to release gas that interferes with transmission of the shock waves.

12. An impact compression apparatus comprising the reusable impact target capsule of claim 3, and a single-stage powder gun, a single-stage gas gun, or gunpowder.

13. The impact compression apparatus of claim 12, wherein the reusable impact target capsule further comprises an impact inducing member.

14. The impact compression apparatus of claim 13, wherein the impact-inducing member has gas holes and/or gas grooves to release gas that interferes with transmission of the shock waves.

* * * * *